United States Patent [19]

Harris

[11] Patent Number: 4,654,899
[45] Date of Patent: Apr. 7, 1987

[54] EYE PROTECTORS

[75] Inventor: Geoffrey W. Harris, Sheffield, United Kingdom

[73] Assignee: National Research Development Corporation, London, England

[21] Appl. No.: 830,877

[22] Filed: Feb. 19, 1986

[30] Foreign Application Priority Data

Feb. 19, 1985 [GB] United Kingdom ............... 8504262

[51] Int. Cl.$^4$ .............................................. A61F 9/02
[52] U.S. Cl. ........................................ 2/436; 2/426
[58] Field of Search ................... 2/436, 426, 428, 435, 2/437, 445, 449

[56] References Cited

U.S. PATENT DOCUMENTS

| 2,881,444 | 4/1959 | Fresh et al. | 2/428 |
| 3,591,864 | 7/1971 | Allsop | 2/436 |
| 3,718,937 | 3/1973 | Smith | 2/436 |
| 4,290,673 | 9/1981 | Yamamoto | 2/437 |

FOREIGN PATENT DOCUMENTS 2018411 10/1971 German Democratic Rep. .... 2/428

Primary Examiner—Werner H. Schroeder
Assistant Examiner—Mary A. Ellis
Attorney, Agent, or Firm—Cushman, Darby & Cushman

[57] ABSTRACT

An eye protector comprising a lens structure for spanning both eyes of a wearer, a circumambient wall member extending rearwardly from said lens structure and such as to leave a substantially unobstructed flow path for air across an interior central zone of the eye protector, and an open fronted, open backed frame member adapted to engage a wearer's face in use, said lens structure being carried by said frame member spaced forwardly from at least a substantial part of the front of the frame member, preferably by integral connection of the top portions of the circumambient wall member and frame member, side portions of the circumambient wall member being disposed laterally beyond said frame member, wherein one or more ventilation apertures are defined between the frame member and the circumambient wall member having a substantially unobstructed area on each side of said central zone of at least 500 mm$^2$.

17 Claims, 2 Drawing Figures

4,654,899 though a central zone above the wearers nose. Since the goggles narrowly enclose the eye areas and only a small area of skin sweats in each cup-shaped structure, the problem of misting is lessened.

EYE PROTECTORS

FIELD OF THE INVENTION

The present invention relates to eye protectors such as goggles.

BACKGROUND TO THE INVENTION

A persistent problem with goggles and with spectacles intended to provide eye protection is their tendency to mist up even under conditions of use that are not particularly arduous. Naturally, the tendency to mist is higher when the wearer is hot and the environment is either cold or damp.

Eye protectors which are substantially enclosed, are frequently provided with ventilating apertures at various positions around their frame periphery but generally these are too small to provide adequate ventilation. In many circumstances, the size of the ventilators is limited by the protective function the eye protectors are required to perform.

In an attempt to provide a sufficient level of ventilation without providing too direct a path for the ingress of dangerous materials, turret ventilators labyrinth ventilators or mesh ventilators are employed. However, we have found that these do little to resist misting, probably because the flow path for air entering and leaving the eye protectors is either too convoluted or too small, giving rise to excessive resistance to flow or produces an air flow pattern in which air travels around the turret or labyrinth and leaves again without effectively sweeping through the eye protector.

Our research indicates that in order to prevent misting an airflow through an eye protector such as a pair of goggles needs to be at the level of 1 liter to 8 liters per minute, the actual flow rate depending upon the operational circumstances prevailing. In normal indoor working environments ambient wind speeds are no greater than 0.1 to 0.2 m per second since higher wind speeds are likely to cause irritation. In order to obtain an adequate flow rate of air, say 3 liters per minute, through goggles at a linear wind speed of say 0.1 m per second the theoretical unrestricted area of access into and subsequently out of goggles or spectacles must be about 500 mm$^2$ per side. A level of over 1000 mm$^2$ per side of the goggles or spectacles would be desirable.

We have found that existing goggles that provide adequate protection do not provide this level of ventilation. Existing goggles often provide areas of ventilation covered with wire mesh or plastics grill which is inadequate often because of the small size of the individual holes, even if their aggregate area is fairly high. The air flow through a mass of small apertures suffers more resistance than that through a larger aperture of the same total area. Except in turbulent conditions, the further the air is from the edge of the aperture through which it flows, the faster it flows. In eye protectors with a large number of small perforations, much of the air flow is slowed by being close to the walls of the perforations.

Moreover, it is often the case that some of the air holes provided are cone shaped with only small exits at the end, some of which are completely sealed over because of poor moulding techniques.

Naturally, it is not possible simply to increase the size of the ventilating holes without rendering eye protectors such as goggles liable to admit foreign material in an undesirable manner.

British Patent Specification No. 371150 discloses a pair of goggles having a pair of lenses each supported on a respective frame structure. The frame structures are mounted on a leather mask. Each eye of the wearer accordingly is covered by a respective cup-shaped structure including a respective lens and air cannot circulate from one side of the face to the other throuh a central zone above the wearers nose. Since the goggles narrowly enclose the eye areas and only a small area of skin sweats in each cup-shaped structure, the problem of misting is lessened.

Ventilation is provided in that each lens is attached to the front of a short cylindrical ring having narrow slots formed around its periphery adjacent the lens, Over the front of the ring is arranged an outer ring which serves to hold the lens in position and to provide an annular shield over the slots. The outer ring forms with the inner ring a thin annular air space which allows air to pass into and out of the air slots after entering the annular space from the rear.

Such an arrangement will not however provide adequate ventilation in practice. Our findings indicate that in this, as in other previous proposals, the ventilation area is inadequate.

Another method of avoiding misting which has been proposed in the past is double glazing the lens or lenses of goggles and spectacles. This may help by raising the temperature of the inner lens but because the double glazed lens unit is thicker overall, it may be that the inner lens is brought closer to the face of the wearer thus decreasing the space within the eye protector through which air may flow. This may even make misting worse rather than better.

Anti-mist treatments for lenses or anti-mist compounds which may be applied to lenses do not prevent condensation. They either convert the condensed moisture into a wet rather than a misted layer or absorb the moisture for a short time. This is only satisfactory where there is an intermittent air flow which at its higher level is sufficient to remove the moisture from the lens.

Accordingly, there is a continuing need for a system of ventilation providing large enough, unobstructed apertures to provide adequate ventilation whilst at the same time providing sufficient protection against penetration of dangerous materials into the goggles in common work situations.

BRIEF DESCRIPTION OF THE INVENTION

The present invention provides an eye protector comprising a lens structure for spanning both eyes of a wearer, a circumambient wall member extending rearwardly from said lens structure and such as to leave a substantially unobstructed flow path for air across an interior central zone of the eye protector, and an open fronted, open backed frame member adapted to engage a wearer's face in use, said lens structure being carried by said frame member spaced forwardly from at least a substantial part of the front of the frame member, side portions of the circumambient wall member being disposed laterally beyond said frame member, wherein one or more ventilation apertures are defined between the frame member and the circumambient wall member having a substantially unobstructed area on each side of said central zone of at least 500 mm$^2$, preferably at least 1000 mm$^2$ per side.

The terms front, back, side, top and bottom used herein to describe and define various features of the eye protectors provided by the invention refer to the eye protectors in the normal wearing position on an erect head.

The lens structure may comprise a one-piece lens member or may define separate lens regions. The eye protector may therefore be a pair of goggles (one lens) or spectacles (two lenses).

Preferably, a top portion of said circumambient wall member is connected to a top portion of said frame member and preferably these portions are integrally connected.

Preferably, a bottom portion of said circumambient wall member is disposed below said frame member.

Preferably, said frame member comprises a portion forming a nose bridge. Preferably, the circumambient wall member comprises a portion forming a nose bridge. Generally there may be nose bridge portions formed by both the circumambient wall member and the frame member, the one lying further down the nose in use than the other.

Preferably, laterally extreme upper and/or lower portions of said circumambient wall member are outwardly flared.

For use by persons not wearing spectacles, it is preferred that the circumambient wall member is relatively shallow and the frame member is relatively deep. For instance, the frame member may be from 50 mm to 70 mm deep at the sides whilst the circumambient wall member may conveniently have sides from 20 mm to 40 mm deep. Particularly preferred depths for the sides of the frame member and the circumambient wall member are about 60 mm and about 30 mm respectively.

When spectacles are worn with such an eye protector however, there is a risk that the spectacles will so close off the front of the open frame member that they will become prone to misting. In such circumstances, it is preferred that the circumambient wall member be relatively deep and the frame member relatively shallow, the dimensions quoted above being effectively reversed. This has the effect of throwing the lenses of the spectacles out in front of the frame member and well into the path of air circulating within the lens member and surrounding wall.

It has been found that such arrangements may render the spectacles less prone to misting than they would be if worn alone by keeping the spectacles at a slightly higher temperature than usual, but maintaining ventilation.

Preferably the inner face of the lens structure is spaced in use from the centre of the wearer's forehead by at least 20 mm. More preferably, the spacing is at least 30 mm. This provides adequate volume within which air may circulate to reduce misting.

All conventional aids to the reduction of misting may be employed such as double glazing, the use of anti-misting surfaces or anti-misting compositions or anti misting lens materials. The use of additional ventilation will generally not be necessary but is not excluded.

For safety, it is preferred that the circumambient wall member project rearwardly from the lens structure sufficiently to overlie a substantial part of the adjacent perimeter of the frame member. Thus, it is best placed to prevent objects penetrating into goggles from the sides or bottom.

BRIEF DESCRIPTION OF THE DRAWING

The invention will be illustrated by the following description of a preferred embodiment with reference to the accompanying drawing in which.

DETAILED DESCRIPTION OF A PREFERRED EMBODIMENT

Figure 1:
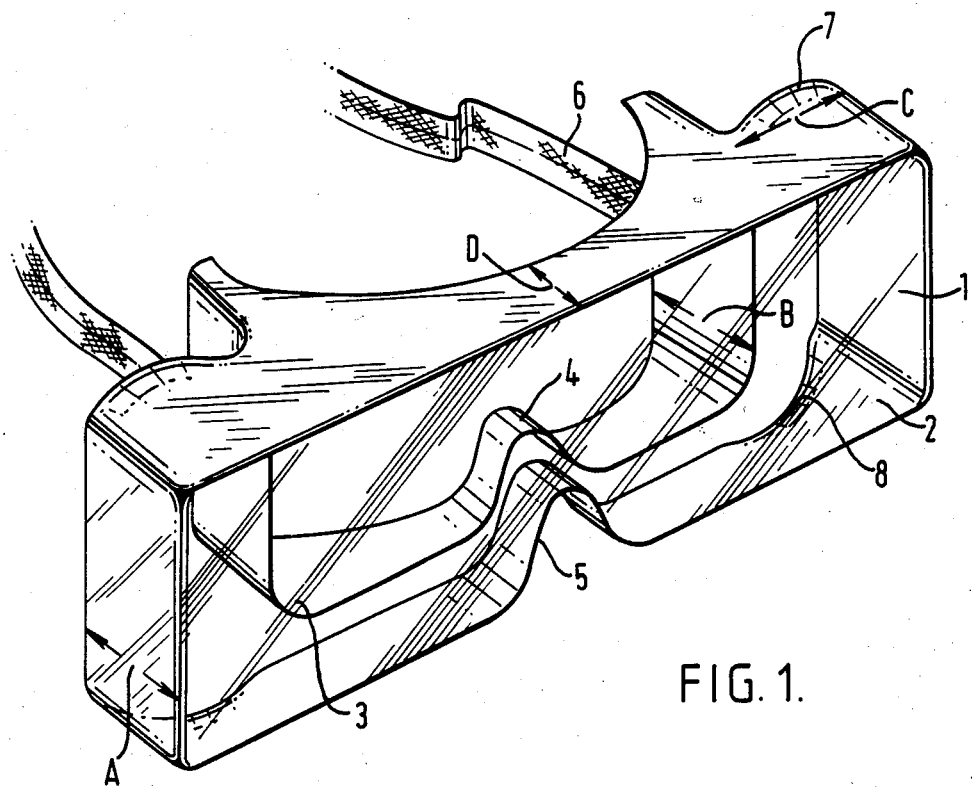
FIG. 1 shows a perspective view of an eye protector according to the invention.

The eye protector comprises a lens structure in the form of a lens member 1 which is double glazed and generally rectangular in form. A circumambient wall member 2 extends rearwardly from the lens member 1 at the bottom, at both sides and at the top.

A frame member 3 comprises a bottom wall, upstanding side walls and a top wall but is open at the back and at the front. The rear perimeter of the frame member 3 is curved to fit snuggly against a wearer's face to form a seal therewith. A central portion of the bottom part of the frame member 3 is formed as a nose bridge 4.

The top of the circumambient wall member 2 is integral with the top part of the frame member 3.

The bottom part of the circumambient wall member 2 is formed as a nose bridge 5 which is spaced from and lies forwardly and below nose bridge 4.

An elastic strap 6 is provided attached to each side part of the frame member 3 for retaining the eye protector on the face of the wearer. Whilst this is the preferred form of attachment, a non-elastic strap or side arms could be employed.

The embodiment shown in particularly suitable for non-spectacle wearer's as the dimension A which is the depth of the side portion of the circumambient wall member 2 is approximately 30 mm whilst the dimension B which is the depth of the side portion of the frame member is approximately 60 mm.

For spectacle wearer's, it is preferred that these dimensions be reversed, the dimension A being approximately 60 mm and the dimension B being approximately 30 mm.

A plane parallel to the lens member 1 but passing through the ends of the circumambient wall side portions cut through the frame member side and bottom walls. Thus, any objects projected at the eye protector directly from the side will not be able to penetrate into the eye protector.

Nonetheless, very extensive ventilation is provided by the gaps between the lens member and its circumambient wall member and the frame member. The lens member is sufficiently wide that it extends laterally beyond the frame member by the distance C which is this case is about 30 mm on each side.

The separation between the inner surface of the inner lens and the rear perimeter of the frame member 3 when the eye protector is in use is indicated by D. This is preferably at least 30 mm.

The rear perimeter of the frame member may be made flexible to assist in providing a comfortable but snug fit.

At each upper corner, the circumambient wall member is upwardly and outwardly flared in a bulge 7. Similarly, at each bottom corner the circumambient wall member is outwardly and downwardly flared in an outwardly projecting bulge 8. This has been found to assist is preventing misting of the lens member.

The eye protector illustrated may be constructed of materials conventionally used such as transparent plastics materials.

It has been found that an eye protector as described and illustrated provides very substantial resistance to misting. Tests have established that an eye protector of this kind does not mist even at a temperature differential between the wearer's skin and the inside of the double glazed lens member of 29° C.

An eye protector as illustrated provides a ventilation area in excess of 1000 mm² per lens side.

To put this in context, those double glazed goggles we have tested mist at differential temperatures as little as 5° C. under comparable test conditions including goggles carrying four turret ventilators.

Viewing the resistance of the goggles to misting from an alternative point of view, the side draught necessary to prevent misting of the eye protector shown under adverse conditions, which in the absence of a draught would cause misting, are considerably lower than those required for other eye protectors.

Since the frame member is relatively deep compared to that of most goggles, it is particularly advantageous to blacken, or in another manner make opaque, the top surface of the frame member to reduce light scattering from the lens.

Whilst the invention has been described with reference to specific characteristics of the preferred embodiment illustrated, many variations and modifications are possible within the scope of the invention.

For instance, as well as the lens member 1 being double glazed, it is possible for some or all of the circumambient wall portion 2 to be double glazed to further insulate the interior of the eye protector from exterior temperatures.

Instead of a one-piece lens being provided by lens member 1, this may comprise separate lenses for each eye supported in a front frame.

One or more grilles or grids may be provided, for instance of wire, across the air flow passage between the frame member and circumambient wall member, provided the flow of ventilating air is not thereby substantially reduced.

Figure 2:
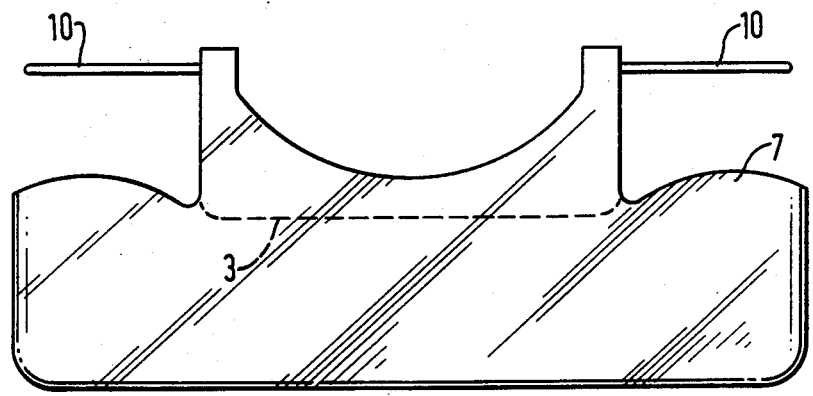
FIG. 2 shows a plan view of a modified version of the eye protector of FIG. 1.

As shown in FIG. 2, a modified version of the goggle as illustrated in FIG. 1 incorporates protection against missiles entering the goggles from the rear of the wearer through the vents and bouncing off the lens into the eyes. The protection takes the form of two vertically running and laterally extending shield wings 10 placed well behind the vents in order to avoid restricting ventilation.

I claim:

1. An eye protector comprising a lens structure for spanning both eyes of a wearer, a circumambient wall member extending rearwardly from said lens structure and such as to leave a substantially unobstructed flow path for air across a central zone of the eye protector, and an open fronted, open backed frame member adapted to engage a wearer's face in use, said lens structure being carried by said frame member spaced forwardly from at least a substantial part of the front of the frame member, said circumambient wall member having side portions disposed laterally beyond said frame member and a bottom portion disposed below said frame member, wherein at least one ventilation aperture is defined between the frame member and the circumambient wall member to provide substantially unobstructed ventilation aperture area on each side of said central zone of at least 500 mm².

2. An eye protector as claimed in claim 1 wherein a top portion of said circumambient wall member is connected to a top portion of said frame member.

3. An eye protector as claimed in claim 1 wherein said frame member comprises a portion forming a nose bridge.

4. An eye protector as claimed in claim 1 wherein said circumambient wall member comprises a portion forming a nose bridge.

5. An eye protector as claimed in claim 1 wherein laterally extreme upper portions of said circumambient wall member are outwardly flared such as to enlarge the volume defined within said circumambient wall member.

6. An eye protector as claimed in claim 1 wherein laterally extreme lower portions of said circumambient wall member are outwardly flared such as to enlarge the volume defined within said circumambient wall member.

7. An eye protector as claimed in claim 1 wherein the circumambient wall member is relatively deep and the frame member is relatively shallow, measured from front to back.

8. An eye protector as claimed in claim 7 wherein the circumambient wall member has side portions from 50 to 70 mm deep and the frame member has side portions from 20 to 40 mm deep.

9. An eye protector as claimed in claim 7 wherein the circumambient wall member has side portions about 60 mm deep and the frame member has side portions about 30 mm deep.

10. An eye protector as claimed in claim 1 wherein the circumambient wall member is relatively shallow and the frame member is relatively deep measured from front to back.

11. An eye protector as claimed in claim 10 wherein the circumambient wall member has side portions from 20 to 40 mm deep and the frame member has side portions from 50 to 70 mm deep.

12. An eye protector as claimed in claim 10 wherein the circumambient wall member has side portions about 30 mm deep and the frame member has side portions about 60 mm deep.

13. An eye protector as claimed in claim 1 wherein the inner face of the lens structure is spaced in use from the centre of the wearer's forehead by at least 20 mm.

14. An eye protector as claimed in claim 1 wherein the inner face of the lens structure is spaced in use from the centre of the wearer's forehead by at least 30 mm.

15. An eye protector as claimed in claim 1 wherein the lens structure is double glazed.

16. An eye protector as claimed in claim 1 wherein the circumambient wall member projects rearwardly from the lens structure sufficiently to overlie a substantial part of the adjacent perimeter of the frame member.

17. An eye protector as claimed in claim 1 wherein on each side of said central zone an aggregate substantially unobstructed ventilation aperture area of at least 1000 mm is provided.

* * * * *